United States Patent
Nashed-Samuel et al.

(10) Patent No.: US 12,251,743 B2
(45) Date of Patent: Mar. 18, 2025

(54) METHOD OF PREVENTING LAMELLAR SILICA FORMATION IN GLASS CONTAINER

(71) Applicant: AMGEN INC., Thousand Oaks, CA (US)

(72) Inventors: Yasser Nashed-Samuel, Thousand Oaks, CA (US); Jeremy Gastwirt, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/643,578

(22) Filed: Apr. 23, 2024

(65) Prior Publication Data

US 2024/0342771 A1    Oct. 17, 2024

Related U.S. Application Data

(62) Division of application No. 16/959,663, filed as application No. PCT/US2019/012119 on Jan. 3, 2019, now Pat. No. 12,042,830.

(Continued)

(51) Int. Cl.
*B08B 9/093* (2006.01)
*A61J 1/06* (2006.01)
(Continued)

(52) U.S. Cl.
CPC ............... *B08B 9/093* (2013.01); *A61J 1/065* (2013.01); *A61J 1/1468* (2015.05); *B08B 17/02* (2013.01);
(Continued)

(58) Field of Classification Search
CPC ........ B08B 9/093; B08B 17/02; A61J 1/1468; A61J 1/065; C03C 23/007; C03C 23/0075;
(Continued)

(56) References Cited

U.S. PATENT DOCUMENTS 5,235,996 A    8/1993    Beswick
2003/0010359 A1    1/2003    Knapp
(Continued)

FOREIGN PATENT DOCUMENTS

WO    WO-2010/038776 A1    4/2010

OTHER PUBLICATIONS

International Search Report and Written Opinion, corresponding International Application No. PCT/US2019/012119, mailing date Apr. 9, 2019.

(Continued)

*Primary Examiner* — Sharidan Carrillo
(74) *Attorney, Agent, or Firm* — MARSHALL, GERSTEIN & BORUN LLP (57) ABSTRACT

Methods of screening a glass container for storing a pharmaceutical formulation for susceptibility to lamellar silica formation includes filling the container with a buffer for the pharmaceutical formulation, storing the container with the buffer and optically analyzing the buffer after storage for one or more particles in the buffer. The one or more particles can be analyzed to determine a morphology and chemical composition and the interior surface of the container, once emptied, can be analyzed for delamination type deformation. The presence of particles in the buffer having a chemical comprising silicon, oxygen, and carbon and the absence of delamination type deformation is indicative of susceptibility to lamellar silica formation.

6 Claims, 6 Drawing Sheets

Related U.S. Application Data (60) Provisional application No. 62/613,173, filed on Jan. 3, 2018.

(51) Int. Cl.

| | |
|---|---|
| A61J 1/14 | (2023.01) |
| B08B 17/02 | (2006.01) |
| C03C 23/00 | (2006.01) |
| G01N 21/90 | (2006.01) |
| G01N 23/2251 | (2018.01) |
| G01N 33/38 | (2006.01) |

(52) U.S. Cl.
CPC ........ *C03C 23/007* (2013.01); *C03C 23/0075* (2013.01); *C03C 23/0085* (2013.01); *G01N 21/9027* (2013.01); *G01N 23/2251* (2013.01); *G01N 33/386* (2013.01); *C11D 2111/18* (2024.01); *G01N 2223/652* (2013.01)

(58) Field of Classification Search
CPC ............ C03C 23/0085; G01N 21/9027; G01N 23/2251; G01N 33/386; G01N 2223/652; C11D 2111/18
See application file for complete search history.

(56) References Cited

U.S. PATENT DOCUMENTS

| | | | |
|---|---|---|---|
| 2014/0154438 A1 | 6/2014 | Sharma et al. | |
| 2014/0370303 A1 | 12/2014 | Jin et al. | |
| 2017/0036950 A1 | 2/2017 | Fadeev et al. | |
| 2018/0067091 A1 | 3/2018 | Burkhalter et al. | |
| 2018/0100846 A1* | 4/2018 | Murphy | A61J 1/1468 |
| 2019/0151334 A1 | 5/2019 | Bosworth et al. | |
| 2021/0078055 A1 | 3/2021 | Nashed-Samuel et al. | |

OTHER PUBLICATIONS

Zai-Qing Wen et al, "Nondestructive detection of glass vial inner surface morphology with differential interference contrast microscopy", Journal of Pharmaceutical Sciences, vol. 101, No. 4, p. 1378-1384, Apr. 1, 2012.
Ennis R D et al, "Glass vials for small vol. parenterals: influence of drug and manufacturing processes on glass delamination", Pharmaceutical Development and Techno, New York, NY, US, vol. 6, No. 3, Aug. 1, 2001.
International Preliminary Report on Patentabillity for Corresponding International Application No. PCT/US2019/021119, dated Jul. 2020.
European Office Action for European Application No. 19703788.0 dated Nov. 8, 2021.
Alberius et al., General Predictive Syntheses of Cubic, Hexagonal, and Lamellar Silica and Titania Mesostructured Thin Films, Chem. Mater., 14:3284-3294 (2002).
Bacon et al., Promotion of attack on glass and silica by citrate and other anions in neutral solution, J. Am. Ceramic. Soc., 42(4):199-205 (1959).
Baillif et al., Dissolution mechanisms of boro-silicate glass fibres in saline solution with added dissolved silica, J. Mater. Sci., 35:967-973 (2000).
Bergna et al., Colloidal silica: Fundamentals and applications. Baton Rouge, Florida: CRC Press, Taylor & Francis.,(2006).
Bohrer et al., Critical evaluation of the standard hydrolytic resistance test for glasses used for containers for blood and parenteral formulations, PDA J. Pharm. Sci. Technol., 58(2):96-105 (2004).
Bunker, Molecular mechanisms for corrosion of silica and silicate glasses, J. Non-Crys. Solids., 179:300-308 (1994).
Cailleteau et al., Insight into silicate-glass corrosion, Nat. Mater., 7(12):978-983 (2008).
Chan, A review on solubility and polymerization of silica, Geothermics, 18(1-2):49-56 (1989).
Clark et al., Corrosion of glass surfaces, Surf. Sci., 100:53-70 (1980).
Conradt, Chemical durability of oxide glasses in aqueous solutions: A review, J. Am. Ceramic. Soc., 91:728-735 (2008).
Crerar et al., Growth and ripening of silica polymers in aqueous solutions, Geochim. Cosmochim. Acta., 45:1259-1266 (1981).
D'Souza et al., Hydroxylation and Dehydroxylation Behavior of Silica Glass Fracture Surfaces, J. Am. Ceram. Soc., 85(6):1499-504 (2002).
Danks et al., The evolution of 'sol-gel' chemistry as a technique for materials synthesis, Mater. Horiz., 3:91-112 (2016).
Das et al., Pharmaceutical packaging technology: A Brief Outline, Res. J. Pharm. Dosage Form. & Tech., 10(1):23-28 (2018).
Dietzel, Impact of cyclic freezing on precipitation of silica in SiO2-H2O systems and geochemical implications for cryosoils and sediments, Chem. Geol., 216(1-2):79-88 (2005).
Dobrucka, Recent trends in packaging systems for pharmaceutical products, LogForum., 10(4):393-398 (2014).
Dove et al., Kinetics of amorphous silica dissolution and the paradox of the silica polymorphs, PNAS., 105(29):9903-9908 (2008).
Fu et al., Silicate, borosilicate, and borate bioactive glass scaffolds with controllable degradation rate for bone tissue engineering applications. II. In vitro and in vivo biological evaluation, J. Biomed. Mater. Res. A, 95(1):172-179 (2010).
Fujimori et al., Development of Conductivity Method as an Alternative to Titration for Hydrolytic Resistance Testing used for Evaluation of Glass Vials Used in Pharmaceutical Industry, PDA J. Pharm. Sci. Tech., 71(1):50-58 (2017).
Guadagnino et al., Delamination propensity of pharmaceutical glass containers by accelerated testing with different extraction media, PDA J. Pharm. Sci. Technol., 66(2):116-125 (2012).
Hench et al., Physical chemistry of glass surfaces, J. Non-Cryst. Solids, 28:83-105 (1978).
Iacocca et al., Corrosive attack of glass by a pharmaceutical compound, J. Mater. Sci., 42(3):801-811 (2007).
Iacocca et al., Factors affecting the chemical durability of glass used in the pharmaceutical industry, AAPS. Pharm.Sci. Tech., 11(3):1340-1349 (2010).
IARC, IARC Monographs on the Evaluation of Carcinogenic Risks to Humans. Volume 81. Man-Made Vitreous Fibres. Lyon, France: World Health Organization, International Agency for Research on Cancer, (2002).
Iler, The Chemistry of Silica: Solubility, Polymerization, Colloid and Surface Properties, and Biochemistry, New York: John Wiley & Sons, (1979).
Jiang et al., Novel Mechanism of Glass Delamination in Type 1A Borosilicate Vials Containing Frozen Protein Formulations, PDA J. Pharm. Sci. Tech., 67(4):323-335 (2013).
Kerwin, Polysorbates 20 and 80 Used in the Formulation of Protein Biotherapeutics: Structure and Degradation Pathways, J. Pharm. Sci., 97(8):2924-2935 (2008).
Kim et al., Robust transparent mesoporous silica membranes as matrices for colorimetric sensors, RSC Adv., 5:16549-16553 (2015).
Kim et al., Synthesis of highly ordered mesoporous silica materials using sodium silicate and amphiphilic block copolymers, Chem. Commun., 1159-1160 (2000).
Kinrade et al., Stable five- and six-coordinated silicate anions in aqueous solution, Science, 285(5433):1542-1545 (1999).
Ledieu et al., Leaching of borosilicate glasses. I. Experiments, J. Non-Cryst. Solids., 343:3-12 (2004).
Lemen et al., Chapter 82. Silica and Silica Compounds, Patty's Toxicology, 5:181-209 (2012).
Mahler et al., Freeze-formed silica fibres, Nature, 285:27-28 (1980).
Makrides et al., Condensation of silica from supersaturated silicic acid solutions, J. Colloid. Interface Sci., 73(2):345-367 (1979).
Molchanov et al., Corrosion of silicate glasses by alkaline solutions, Chem. Bull., 6(10):1179-1184 (1957).
Narhi et al., Classification of protein aggregates, J. Pharm. Sci., 101(2):493-498 (2012).
NASA, A Review on Pharmaceutical Packaging Material, World Journal of Pharmaceutical Research, 3(5):344-368 (2014).
Perera et al., Dissolution rates of silicate glasses in water at pH 7, J. Am. Ceram. Soc., 74(6):1269-1274 (1991).

(56) References Cited

OTHER PUBLICATIONS

Porter, Handbook of Surfactants. 2nd ed. Glasgow: Blackie Academic & Professional, (1994).
Rajabipour et al., Alkali-silica reaction: Current understanding of the reaction mechanisms and the knowledge gaps, Cement and Concrete Research, 76:130-146 (2015).
Randolph, Surfactant-protein interactions, Pharm. Biotechnol., 13:159-175 (2002).
Ratnaswamy et al., A Case Study of Nondelamination Glass Dissolution Resulting in Visible Particles: Implications for Neutral pH Formulations, J. Pharm. Sci., 103:1104-1114 (2014).
Schaut et al., A New Glass Option for Parenteral Packaging, PDA J. Pharm. Sci. Tech., 68(5):527-534 (2014).
Schloze, Chemical durability of glasses, J. Non-Cryst. Solids, 52(1-3):91-103 (1982).
Schramm, Surfactants and their solutions: Basic principles. In: Schramm LL, editor. Surfactants: Fundamentals and applications in the petroleum industry. 1st ed. Cambridge: University Press. pp 1-49, (2000).
Sjöberg, Silica in aqueous environments, J. Non-Cryst. Solids, 196:51-57 (1996).
Sloey et al., An Evaluation of the Glass Vial Hydrolytic Resistance Method, PDA J. Pharm. Sci. Tech., 73(3):212-219 (2019).
Sloey et al., Determining the delamination propensity of pharmaceutical glass vials using a direct stress method, PDA J. Pharm. Sci. Technol., 67(1):35-42 (2013).
Tarutani, Polymerization of silicic acid, a review, Anal. Sci., 5(3):245-252 (1989).
USP, <1660> Evaluation of the inner surface durability of glass containers, (2012).
Warring et al., Adsorption of a Polyethoxylated Surfactant from Aqueous Solution to Silica Nanoparticle Films Studied with In Situ Attenuated Total Reflection Infrared Spectroscopy and Colloid Probe Atomic Force Microscopy, Langmuir, 34(45):13481-13490 (2018).
Wen et al., Glass Particle Formation and Delamination in Pharmaceutical Glass Vials, Biopharma., (2019).
Wirth et al., The initial kinetics of the dissolution of vitreous silica in aqueous media, J. Colloid. Interface. Sci., 68(3):492-500 (1978).
Zolls et al., Particles in therapeutic protein formulations, Part 1: Overview of analytical methods, J. Pharm. Sci., 101(3):914-935 (2012).

* cited by examiner

Rolled/twisted

FIGURE 2B

Rod-Like

METHOD OF PREVENTING LAMELLAR SILICA FORMATION IN GLASS CONTAINER

CROSS-REFERENCE TO RELATED APPLICATIONS

The present application is a divisional application of U.S. patent application Ser. No. 16/959,663 filed Jul. 1, 2020 now U.S. Pat. No. 12,042,830, which is a U.S. national stage of International Patent Application No. PCT/US2019/012119 filed Jan. 3, 2019, which claims the benefit of U.S. Provisional Application 62/613,173 filed on Jan. 3, 2018, the disclosures of which are incorporated herein by reference in their entireties.

BACKGROUND

Field of the Disclosure

The present disclosure relates generally to a method of preventing lamellar silica formation in a glass container storing a pharmaceutical formulation and methods for screening for such formation in a stored pharmaceutical formulation.

BRIEF DESCRIPTION OF RELATED TECHNOLOGY

The packaging of pharmaceutical products plays a very important role in the preservation of the quality, sterility, and activity of a drug product. The packaging chosen for the pharmaceutical formulation must protect against adverse external influences that may alter the properties of the composition (e.g. moisture, light, oxygen, temperature variations, etc.), in addition to protecting against biological contamination and physical damage. Furthermore, the packaging chosen for a particular pharmaceutical formulation must not have an adverse effect or interaction with the drug product itself or other components of the composition. Such interactions can include chemical interactions of the composition with the surface of the package, or leaching of the packaging materials into the contained pharmaceutical formulation.

Pharmaceutical formulations can be contained in numerous forms of packaging, such as ampoules, bags, bottles, needles, syringes, or vials. Most commonly used in parenteral formulations are glass vials. Glass vials generally include a stopper and overseal, and the contents are removed after the stopper is pierced. These vials can be for multi-dose or single-dose products. Three main types of glass for pharmaceutical formulations and/or products exist. Type 1 glass, also known as "body neutral," is a borosilicate glass known to have good chemical resistance. Type 2 glass has a treatment applied to the internal surface of the glass to reduce ion exchange, and is typically used for glass infusion bottles. Type 3 glass is a soda-lime glass and is the most commonly manufactured glass. It is generally used for storing tablets and other solid or powdered pharmaceuticals. Of the three types, Type 1 is most commonly used for liquid and aqueous-form pharmaceutical products.

Glass vials and other pharmaceutical packages must undergo effective washing procedures prior to being filled with a pharmaceutical formulation in order to remove any residues or contaminants on the glass surface from the manufacturer or shipping. Conventional washing procedures typically include rinsing the vials with a pressurized jet of sterile Water for Injection (WFI), followed by drying and depyrogenation. Depyrogenation is the process in which glass vials are subjected to an increased or ramped rate of heat in order to remove bacterial pyrogens, such as endotoxins and exotoxins, from the surface of the vial. Typically, depyrogenation of glass vials is completed at 250° C. After depyrogenation, the vials are ready to be filled with the pharmaceutical formulation.

A common adverse interaction between a pharmaceutical composition and glass vial is glass delamination, which results in visible glassy flakes or particles in the pharmaceutical formulation, affecting the safety and stability of the product.

In traditional glass delamination, when glass vials are filled with the liquid pharmaceutical formulation, an "altered" silicon oxide (i.e. silica) layer that is subject to strong re-hydration and swelling forms on the interior of the glass container and leaches into the solution contained within the glass container to form glassy flakes, or glass lamellae. As these silica particles leach, they leave the glass interior less resistant to chemical attack, and contribute to the formation of cracks and fissures on the surface of the glass. This process is also referred to as weathering. The chemical composition and visual appearance of glassy flakes resulting from glass delamination have unique properties that allows for their identification and differentiation from other foreign and/or protein matter. Conventional techniques for combating glass delamination include reformulating the pharmaceutical compositions, changing the type of container used to contain the pharmaceutical composition to one with a low alkali content, treating the surfaces of glass containers with materials such as ammonium sulfate to reduce erosion, and reevaluating the storage conditions (i.e. temperature and/or shelf-life) of the filled glass container.

SUMMARY

A method in accordance with an embodiment of the disclosure for preventing lamellar silica formation in a borosilicate glass container storing a pharmaceutical formulation in an interior of the glass container, includes, prior to filling the glass container with the pharmaceutical formulation, washing the interior of the glass container with a pressurized water jet, and drying the glass container by blowing compressed air into the interior of the glass container for at least 3000 ms wherein the glass container is washed and dried using a batch washer.

A method in accordance with an embodiment of the disclosure for preventing lamellar silica formation in a borosilicate glass container storing a pharmaceutical formulation in an interior of the glass container, includes, prior to filling the glass container with the pharmaceutical formulation, washing the glass container with a pressurized water jet under conditions sufficient to remove contaminants, drying the washed glass container, and depyrogenizing the glass container by heating the dried glass container in an oven at a temperature of at least about 250° C., wherein the glass container remains stationary in the oven during heating.

A method in accordance with yet another embodiment of the disclosure of preventing lamellar silica formation in a borosilicate glass container containing a pharmaceutical formulation in an interior of the glass container, includes, prior to filling the glass container with the pharmaceutical formulation, washing the glass container with a pressurized water jet under conditions sufficient to remove contaminants, drying the washed glass container by blowing compressed air into the interior of the glass container for at least 3000 ms, placing the dried glass container in a heat-safe container and covering the heat-safe container containing the dried glass container with a lid, and depyrogenizing the dried glass container contained in the covered heat-safe container.

A method of screening a glass container storing a pharmaceutical formulation for susceptibility to lamellar silica formation when filled with a pharmaceutical formulation, in accordance with an embodiment of the disclosure, includes filling a washed and depyrogenized glass container with a pharmaceutical formulation, wherein the glass container comprises ions selected from the group comprising sodium, calcium, hydroxide, silicate, and combinations thereof, storing the filled glass containers at a temperature of 40° C. for at least 14 days, optically analyzing the pharmaceutical formulation after storage for formation of particles in the formulation, when particle formation is observed, isolating the particles from the formulation for structural and elemental analysis, analyzing the isolated particles using one or more of optical microscopy, scanning electron microscopy/energy dispersive X-ray spectroscopy (SEM/EDS), Fourier-transform infrared spectroscopy (FTIR), x-ray photoelectron spectroscopy (XPS), differential interference contrast microscopy (DIC), microflow imaging (MFI), and combinations thereof to determine a morphology of the particles and the presence of silicon, wherein a glass container is considered susceptible to lamellar silica formation where the isolated particles are determined to have a flake-like morphology and the presence of silicon is detected in the particles.

For the methods described herein, optional features and conditions are contemplated to be selected from the various aspects, embodiments, and examples provided herein.

Further aspects and advantages will be apparent to those of ordinary skill in the art from a review of the following detailed description. While the method of preventing lamellar formation and the method of screening a glass container for susceptibility to lamellar silica formation are susceptible of embodiments in various forms, the description hereafter includes specific embodiments with the understanding that the disclosure is illustrative, and is not intended to limit the invention to the specific embodiments described herein.

DETAILED DESCRIPTION

A silica-based contaminant that is distinct from glass delamination has been found to be associated with storage of certain pharmaceutical formulations in borosilicate type glass. The silica-based contaminant, lamellar silica, is a flake-like contaminant that forms in pharmaceutical formulations over storage time. Significantly, unlike glass delamination, there is no etching or other disruption or visible alternation seen on the glass container interior surface. The appearance of glass lamellae from glass delamination is known to follow Arrhenius kinetics, that is, as temperature increases, the rate of formation of glass lamellae increases. In other words, over time, the number of glass lamellae particles in the pharmaceutical formulation increases. Lamellar silica formation does not follow this same kinetics pathway. Instead, glass containers affected by lamellar silica show the formation of a finite number of particles that typically does not increase over time. Furthermore, the particle morphology and chemical composition of glass lamellae and lamellar silica are distinct. While both types of particles similarly comprise silicon and oxygen, glass lamellae are dense, amorphous particles that are translucent to white in appearance. In contrast, lamellar silica are thin, two-dimensional, flat particles that reflect light, making them visually distinct from glass lamellae. In addition to silicon and oxygen, lamellar silica further comprises an organic component, such as carbon, distinguishing it from glass lamellae.

It has been found that a number of factors contribute and exacerbate the formation of lamellar silica, including for example, the composition of the glass container, the methods used to prepare the glass container prior to filling it with a pharmaceutical formulation, and also the pharmaceutical formulation itself. Without intending to be bound by theory, it is believed that the lamellar silica formation results from the interaction of the pharmaceutical formulation with the inner glass surface, which can have a silica gel leachable layer resulting from standard washing and drying procedures. In particular, during conventional and standard batch washing and drying procedures, moisture remaining on the glass surface after drying can react with the alkali and alkaline ions in the composition of the borosilicate glass container, such as sodium and calcium, forming hydroxyl groups on the surface of the glass. Generally, depyrogenation does not remove the hydroxyl groups immediately because the heat is typically ramped from about room temperature to at least about 250° C. The hydroxyls, therefore, can cause the formation of silica gel on the glass surface. When the glass containers are subsequently filled with the pharmaceutical formulation, silicates and silicic acid from the silica gel can leach into the contained pharmaceutical formulation, and using the components within the pharmaceutical formulation as template, aggregate into lamellar silica. It has also been found that other formulation components such as acidic buffers can contribute to the silica leaching.

Methods of preventing the formation of lamellar silica in glass containers used for storing pharmaceutical formulations through modification of the washing, drying, and/or depyrogenation steps are disclosed herein. It has been advantageously found that methods in accordance with the disclosure can prevent or reduce lamellar silica formation in stored formulations otherwise susceptible to such formation by increasing the drying time in a batch process to at least 3000 ms. Without intending to be bound by theory, the additional drying is believed to remove residual hydroxyl groups that can react with the glass surface during conventional depyrogenation at 250° C. to form a leachable silica layer. In alternatively embodiments, it has been found that depyrogenizing at increased temperatures above 250° C. and approaching annealing at temperatures can also result in destruction of hydroxyls, preventing formation of the leachable silica layer.

Glass Container

The glass container can be a type 1 borosilicate glass, or type 1b. As compared to other types of glass, type 1b glass contains significant amounts of boric oxide, aluminum oxide, and alkali and/or alkaline earth oxides. It has a high hydrolytic resistance and a high thermal shock resistance due to its chemical composition. Type 1b glass containers can be, in some embodiments, delamination controlled type glass containers. That is, glass containers used in accordance with embodiments of the disclosure can be manufactured to prevent glass delamination. Glass containers that are delamination controlled generally show a unique surface homogeneity and chemical stability, improving the interior surface liability to delamination. It has been found, however, that despite this improved stability against glass delamination, such containers can still remain susceptible to lamellar silica formation when storing certain pharmaceutical formulations.

Glass, in its pure form, consists of silicon dioxide and has a melting point in excess of 1500° C. Due to this extreme temperature, pure glass is rarely used commercially. Instead, network modifiers such as sodium, potassium, calcium, barium, and/or magnesium are added to the glass to lower the melting point of the glass to allow for processing into shapes, such as vials. Consequently, these network modifiers compromise the chemical durability of the glass. Therefore, in addition to network modifiers, network stabilizers, such as boron and aluminum oxides, are added to improve the durability of the glass. Each of these components, in addition to the silicon dioxide itself, is a potential source for leaching.

Glass compositions do not exist as stoichiometric chemical compounds, but rather are expressed as a range of components, allowing for variability in the chemical makeup of each article of glass depending on lot and manufacturer. Type 1b borosilicate glass generally contains about 65 to about 82 wt % silicon dioxide, about 5 to about 13 wt % boric oxide, about 2 to about 9 wt % aluminum oxide, about 3 to about 12 wt % sodium and potassium oxides and about 0 to about 6 wt % calcium, magnesium, and barium oxides. A commercially available Type 1b vial that can be used in methods in accordance with the invention is TOPLINE® SCHOTT Vials DC (Schott Pharmaceutical Services).

When formed into glass containers used to contain pharmaceutical formulations, such as vials, tubes, or ampoules, the glass is heated to temperatures sufficient to mold the glass into the desired shape. The glass is then annealed at a temperature approximately 20 to 30° C. above its transformation, or glass transition temperature, in order to enhance the mechanical and chemical durability of the glass. For type 1b borosilicate glass, the annealing temperature is approximately 600° C.

The glass containers used in accordance with the methods of the disclosure can be any size and shape. For example, in various embodiments, the glass container is a glass vial having a volume of about 10 cc to about 100 cc, about 25 cc to about 75 cc, or about 40 cc to about 60 cc. For example, glass vials having volumes of about 10, 15, 20, 25, 30, 35, 40, 45, 50, 50, 55, 60, 65, 70, 75, 80, 85, 90, 95, or 100 cc can be used. In various embodiments, the glass container has a volume of 10 cc. In other embodiments, the glass container has a volume of 50 cc.

Washing and Drying Batch Process

It is standard practice in the pharmaceutical industry that all glass containers used for containing and/or storing a pharmaceutical formulation are washed prior to being filled with the composition. Washing and drying procedures can be accomplished using what is known in the art as batch processing or can be accomplished using a continuous or tunnel process. Methods in accordance with the disclosure utilize a batch process.

In a batch process, washing and drying of the glass container are completed in discrete and intermittent steps. Depyrogenizing can also be part of the batch process. During the washing step of a batch process, the glass containers are contained within a larger wash vessel and washed while held stationary. Similarly, during drying, the glass containers are contained in a vessel and held stationary during drying. The depyrogenizing step in a batch process can be achieved in an oven while the containers are contained in a heat safe container and are stationary in the oven. In various embodiments, the glass containers can be in a covered vessel during the depyrogenation step. In contrast with a continuous, or tunnel, process, the transition between the washing and drying phase and the depyrogenizing phase requires the manual transfer of the glass container from a batch washer to an oven. A continuous or tunnel process also keeps the glass containers in continuous motion through the washing, drying, and depyrogenation tunnel.

A method of preventing the formation of lamellar silica in accordance with the disclosure can include washing and drying the glass containers in a batch process. For example, in a batch process, one or more glass containers are placed on a tray or other vessel, inserted into a batch washer, washed while stationary using water, dried while stationary using air or other inert gas, and manually removed from the batch washer. The number of glass containers that can be washed and subsequently dried in the batch washer is not particularly limiting, and depends on the size of the tray and/or the size of the batch washer. For example, the number of glass containers that can be simultaneously washed and dried can be in a range between about 1 glass container and about 10,000 glass containers, about 100 glass containers and about 7500 glass containers, about 500 glass containers and about 5000 glass containers, about 1000 glass containers and about 4000 glass containers, or about 2000 glass containers and about 3000 glass containers, for example about 1, 10, 100, 250, 500, 750, 1000, 1500, 2000, 2500, 3000, 3500, 4000, 4500, 5000, 5500, 6000, 6500, 7000, 7500, 8000, 8500, 9000, 9500, or 10,000 glass containers.

In embodiments, after the glass container is washed and dried, the glass container may be placed in a heat-safe container for depyrogenation. The heat-safe container containing the dried glass container can then be covered with a lid and placed in an oven for depyrogenation. Any suitable type and size of the heat-safe container can be used. For example, conventional batch processing utilizes stainless steel containers, which can also be used in methods in accordance with the disclosure.

Washing of the Glass

Methods of preventing lamellar silica formation in accordance with embodiments of the disclosure include washing the glass container with water. The can be, for example, in the form of a pressurized water jet. As used herein, "wash" and "rinse" are used interchangeably to refer to the process of exposing the interior surface of the glass container to the water to clear dust or other containments prior to filling. Water for Injection (WFI) or other suitable water sources can be used for the washing step. WFI is conventionally used in washing glass containers in pharmaceutical processing as it is a sterile, nonpyrogenic preparation of water which contains no bacteriostat, antimicrobial agent, or added buffer.

In various embodiments using a pressurized water jet, the water pressure can be about 5 psi to about 50 psi, about 10 psi to about 45 psi, about 15 psi to about 35 psi, or about 20 psi to about 30 psi. Other suitable water pressures include for example, about 5, 6, 7, 7.25, 8, 9, 10, 11, 12, 13, 14, 15, 16, 17, 18, 19, 20, 22, 24, 26, 28, 30, 32, 34, 36, 38, 40, 42, 44, 45, 46, 48, or 50 psi. In various embodiments, the pressure of the pressurized water jet is at least about 7.25 psi. In alternative embodiments, the glass container is washed with a pressurized water jet under conditions sufficient to remove contaminants. These conditions include, but are not limited to, factors such as the pressure of the pressurized water jet, the temperature of the pressurized water jet, the duration of the washing cycle, the number of washing cycles, and any combination of the foregoing.

The water used for washing can be heated in some embodiments. The temperature of the water used for the washing of the glass containers can be about 20° C. to about 90° C., about 30° C. to about 85° C., about 50° C. to about 80° C., about 70° C. to about 80° C., or about 70° C. to about 75° C. Other suitable temperatures include, for example, about 20, 25, 30, 35, 40, 45, 50, 55, 60, 65, 70, 71, 72, 73, 74, 75, 76, 77, 78, 79, 80, 85, or 90° C. In various embodiments, the washing step includes use of a pressurized water jet at a temperature of at least about 72° C.

The methods of the disclosure can utilize one or more wash cycles. As used herein, a "washing cycle" is a discrete length of time that the interior of a glass container is exposed to a stream of pressurized water. That is, between each washing cycle, there is a period of time during which the glass container is not exposed to the pressurized water jet.

The glass containers may undergo 1 washing cycle to about 10 washing cycles, about 2 washing cycles to about 8 washing cycles, about 3 washing cycles to about 6 washing cycles. Other suitable numbers of wash cycles include about 1, 2, 3, 4, 5, 6, 7, 8, 9, or 10 wash cycles. In an embodiment, the glass container undergoes about 4 washing cycles. In another embodiment, the glass container undergoes at least 3 washing cycles.

In a conventional batch process, the wash cycle is typically about 1000 ms. In the methods in accordance with the disclosure, each wash cycle can have a duration of about 500 ms to about 6000 ms, about 1000 ms to about 5000 ms, about 2000 ms to about 4500 ms, about 3000 ms to about 6000 ms, or about 3000 ms to about 4000 ms. Other suitable durations include about 500, 1000, 1200, 1400, 1600, 1800, 2000, 2200, 2400, 2600, 2800, 3000, 3200, 3400, 3600, 3800, 4000, 4200, 4400, 4600, 4800, 5000, 5200, 5400, 5600, 5800, or 6000 ms. In embodiments, the duration of the washing cycle is at least about 1000 ms. In embodiments, the duration of the wash cycle is greater than 1000 ms. In embodiments, the duration of the washing cycle is greater than 1000 ms to about 6000 ms. In various embodiments, wash cycles each having the same duration can be used. In other embodiments, wash cycles having different durations can be used.

In an embodiment, the glass container is washed using at least 3 washing cycles, wherein each washing cycle is greater than 1000 ms. In embodiments, the glass container is washed using 3 to 10 washing cycles, wherein each washing cycle is greater than 1000 ms. In one embodiment, the glass container is washed using at least 4 washing cycles, each cycle lasting about 1000 ms with a pressurized WFI water jet of at least 72° C. and at least 10 psi.

The same duration can be used in various embodiments for different volume-sized containers, for example for 10 cc volume glass containers and 50 cc volume glass containers. For example, in an embodiment, a 10 cc glass container or a 50 cc glass container can be washed by exposing the interior of the glass container to pressurized water for at least 3000 ms. In some embodiments, depending on the size and/or shape of the glass container used, it may be advantageous to tailor the wash time to the container.

Drying of the Glass

The method preventing lamellar silica formation in accordance with the disclosure further includes a drying step performed after washing. As discussed above, it has been advantageously found that formation of lamella silica in stored formulations otherwise susceptible to such formation can be reduced or prevented by extending the drying duration.

The glass container can be dried by blowing air or other suitable inert gas into the interior of the glass container. For example, the air can be compressed air. For ease of reference, the drying step will be described with reference to air or compressed air, but it should be understood herein that other inert gases can be suitably used. The pressure of the compressed air or inert gas can range from about 10 psi to about 70 psi, about 20 psi to about 60 psi, about 30 psi to about 50 psi, or about 40 psi to about 50 psi. Other suitable pressures include, for example, about 10, 12, 14, 14.5, 16, 18, 20, 22, 24, 26, 28, 30, 32, 34, 36, 38, 40, 42, 44, 46, 48, 50, 52, 54, 56, 58, 60, 62, 64, 66, 68 or 70 psi. In embodiments, the pressure of the compressed air is at least about 14.5 psi. The air used for drying can be ambient temperature. It has been found that use of heated air during drying can be disadvantageous as it can increase humidity and reduce the effectiveness of the drying.

As with the washing step, the drying step can include one or more drying cycles. As used herein, a "drying cycle" is the length of time that the interior of a glass container is consistently blown with air. That is, between each drying cycle, there is a period of time during which the glass container is not exposed to the air. The duration of a single drying cycle can range from about 3000 ms to about 10,000 ms, about 3000 ms to about 8000 ms, about 3000 ms to about 7000 ms, about 3000 ms to about 6000 ms, about 4000 ms to about 6000 ms, or about 4500 ms to about 5500 ms. Other suitable drying times include, for example about 3000, 3500, 4000, 4500, 5000, 5500, 6000, 6500, 7000, 7500, 8000, 8500, 9000, 9500, or 10,000 ms. In various embodiments, the duration of the drying cycle is at least about 3000 ms. In another embodiment, the duration of the drying cycle is about 6000 ms.

The glass container may undergo one or more drying cycles, for example, about 1 cycle to about 15 cycles, about 2 cycles to about 14 cycles, about 4 cycles to about 10 cycles, or about 6 cycles to about 8 cycles. Other suitable numbers of dry cycles include about 1, 2, 3, 4, 5, 6, 7, 8, 9, 10, 11, 12, 13, 14, or 15 cycles. The drying cycles, when multiple are used, can have the same or different durations.

In various embodiments, the drying step includes at least 3 drying cycles, each drying cycle comprising blowing compressed air into the interior of the glass container for about 3000 ms. In various embodiments, the glass container undergoes between 3 and 10 drying cycles, each drying cycle comprising blowing compressed air into the interior of the glass container for at least 3000 ms.

The same duration can be used in various embodiments for different volume-sized containers, for example for 10 cc volume glass containers and 50 cc volume glass containers.

For example, in an embodiment, a 10 cc glass container or a 50 cc glass container can be dried by blowing compressed air into the interior of the glass container for about 3000 ms to about 6000 ms. In another embodiment, a 10 cc glass container or a 50 cc glass container can be dried by blowing compressed air into the interior of the glass container for about 5000 ms to about 8000 ms. In some embodiments, depending on the size and/or shape of the glass container used, it may be advantageous to tailor the dry time to the container Depyrogenation In some embodiments, the glass container undergoes depyrogenation. Depyrogenation is a process used to prepare glass containers for aseptic filling. Depyrogenation is distinct from sterilization, as it uses heat to destroy the endotoxins that sterilization cannot kill. Depyrogenation by dry heat is the most common process used to prepare pharmaceutical products. Depyrogenation is conventionally done at a temperature of about 200° C. for about 30 minutes or at about 250° C. for about 60 minutes. In various embodiments, the methods can use conventional depyrogenation. It has also been found, however, that lamellar silica formation can be prevented by using increased depyrogenation temperature. For example, depyrogenation at temperatures greater than 250° C. can reduce or eliminate lamellar silica formation with or without the additional drying used in various methods in accordance with the disclosure. In various embodiments, the depyrogenation temperature can be about 150° C. to about 600° C., about 180° C. to about 400° C., about 200° C. to about 350° C., about 250° C. to about 330° C., or about 330° C. to about 350° C. Other suitable temperatures include, for example, 150, 160, 180, 200, 225, 250, 275, 300, 325, 330, 350, 375, 400, 425, 450, 475, 500, 525, 550, 575, or 600° C.

The dry heat of the depyrogenation step can be ramped from ambient or an elevated oven temperature to the depyrogenation temperature at a rate of about 1.5° C./min. In some embodiments, the glass containers are held in the depyrogenation oven at elevated temperatures before the start of the depyrogenation cycle. For example, in some embodiments, the containers may be held at a temperature of about 90° C. for about 60 minutes prior to the start of the depyrogenation cycle. As used herein, the "depyrogenation cycle" begins when the temperature begins to ramp from ambient temperature at a rate of about 1.5° C./min and is complete when, after the glass container is held at the depyrogenation temperature for a period of time, the temperature is ramped down at a rate of about 1.5° C./min to ambient temperature. In embodiments, the glass container may be held at the depyrogenation temperature for about 30 minutes to about 150 minutes, about 45 minutes to about 135 minutes, about 60 minutes to about 120 minutes, or about 90 minutes to about 105 minutes, for example about 30, 35, 40, 45, 50, 55, 60, 65, 70, 75, 80, 85, 90, 95, 100, 105, 110, 115, 120, 130, 140, or 150 minutes. In preferred embodiments, the interior surface of the glass container is substantially free of a silica gel after depyrogenation.

Pharmaceutical Formulation

The pharmaceutical formulation contained within the glass container can affect or contributed to the formation of lamellar silica. For example, formulations having certain components as discussed herein may have an increased tendency or risk for lamellar silica formation. Without intending to be bound by theory, it is believed, that the combination of the stored pharmaceutical formulations and the type of glass vial contribute to the susceptibility of the formation of lamellar silica. As noted above, borosilicate glass has been found to be susceptible to lamellar silica when washed using batch conditions and storing a pharmaceutical formulation having an acidic or chelating component and a template component. Without intending to be bound by theory, it is believed that an acid component, such as an acid buffer, or other component that is a chelating agent, within the pharmaceutical formulation interacts with the glass surface to release silica into the solution, which formed during conventional batch wash, dry, and depyrogenation conditions. It is further believed that, the template component within the formulation, allow the leached silica to aggregate to form into lamellar silica.

The formulations can have various active ingredients including proteins, antibodies, small molecule drugs, and the like. Such active ingredients can serve as template components in various embodiments. For example, in various embodiments, the formulation can include an anti-CD20 antibody. Commercially available anti-CD20 antibodies, such as rituximab, obinutuzumab, ofatumumab, Ibritumomab tiuxetan, and tositumomab, can be included in the formulations for example. Other active ingredients that may be included in the pharmaceutical composition include, but are not limited to, melphalan, piperacillin, tazobactam, vecuronium bromide, and etoposide.

The pharmaceutical formulation that are more susceptible to lamellar silica formulation can further include an acidic or chelating buffering agent. It has been found that acidic and chelating buffering agents can increase the risk of lamellar silica formation due to the potential interaction of the buffer with a silica gel layer formed on the glass surface during conventional wash/dry/depyrogenation that results in leaching of the silica. Examples of buffering agents that enhance susceptibility to lamellar silica formulation include, but are not limited to citric acid, phosphoric acid, acetic acid, succinic acid, gluconic acid, glutamic acid, tartaric acid, benzoic acid, lactic acid, phosphoric acid, maleic acid, aspartic acid, carbonic acid, histidine, and other organic acids, or salts thereof may contribute to the formation of lamellar silica in conventionally washed glass containers. In an embodiment, the pharmaceutical formulation contained in or to be contained in the glass container includes citric acid.

Suitable concentrations of the buffering agent may be about 1 mM to about 50 mM, about 5 mM to about 40 mM, about 10 mM to about 30 mM, or about 15 mM to about 25 mM, for example, about 1, 5, 10, 12, 15, 18, 20, 21, 22, 23, 24, 25, 26, 27, 28, 29, 30, 32, 35, 38, 40, 45, or 50 mM. In embodiments, the concentration of the buffering agent is about 25 mM.

It has been found that pharmaceutical formulations having higher pH levels can be more susceptible to the formation of lamellar silica, particularly in borosilicate glass containers. The pH of a pharmaceutical formulation more susceptible to lamellar silica formation can be in a range of about 4.5 to about 8.0, about 5.0 to about 8.0, or about 6.0 to about 8.0, for example, about 4.5, about 5.0, about 5.5, about 6.0, about 6.5, about 7.0, about 7.5, or about 8.0. In embodiments, the pharmaceutical formulation has a pH of about 6.0 to about 8.0. For example, the pharmaceutical formulation in various embodiments can have a pH above about 6.2. In an embodiment, the pharmaceutical formulation has a pH of about 6.5.

Pharmaceutical formulations susceptible to lamellar silica formation during storage include a component that serves as a template upon which the leached silica can aggregate to form the lamellar silica flake. In various formulations, the active ingredient, such as a protein or antibody can serve as the template. A pharmaceutical excipient in the formulation could also serve as the template. For example, pharmaceutical excipients such as nonionic surfactants, anionic surfactants, cationic surfactants, polyols, monosaccharides, polysaccharides, phospholipids, and combinations thereof could act as templates. More specifically, pharmaceutical excipients such as polysorbate 80, polysorbate 20, hyaluronic acid, pluronic acid, sodium alginate, gelatin, chitosan, lecithin, mannitol, sucrose, sulfobutylether beta cyclodextrin, sodium chloride, and combinations thereof may serve as a template. For example a formulation susceptible to lamellar silica formation can include polysorbate 80.

Prevention of Lamellar Silica

Prevention of lamellar silica can be tested or confirmed by storage of the pharmaceutical formulation in a glass container treated in accordance with the methods of the disclosure at standard or accelerated conditions. A stored pharmaceutical formulation is considered to be at low or no risk for lamellar silica formation under normal storage conditions over the shelf-life of the product if it remains free of such formation under accelerated storage conditions of 40° C. for 30 days. For example, a product that is stored at 2° C. to 8° C. under normal conditions should remain free of lamellar silica over the entire shelf life, when passing under the accelerated storage conditions, for example, for 30 days. Testing for lamellar silica can include monitoring stored vials at various time points, such as 1 day, 2 days, 5 days, 10 days, 15 days, 30 days, 45 days, 60 days, 75 days, 90 days, 100 days, 120 days, 150 days, or 180 days.

Accelerated storage conditions can also be achieved by spiking the formulation with a source of elemental silicon. For example, a formulation that is spiked such that the formulation has a concentration of about 5 to about 30 ppm elemental silicon should remain free of lamellar silica after storage under normal conditions or accelerated 40° C. storage for at least 1 day, at least 2 days, at least 5 days, at least 7 days, at least 10 days, at least 14 days, at least 15 days, at least 20 days, at least 25 days, or at least 30 days.

Method of Screening

Also disclosed herein is a method of screening a glass container storing a pharmaceutical formulation for susceptibility to lamellar silica formation when filled with a pharmaceutical formulation.

The method of screening comprises filling a washed, dried, and depyrogenized glass container with a pharmaceutical formulation with or without the active component. The glass container to be screened for susceptibility for a given formulation comprises ions selected from the group consisting of sodium, calcium, hydroxide, silicate, and combinations thereof. In embodiments, the glass container is a borosilicate glass container.

In general, pharmaceutical formulations that are considered susceptible to lamellar silica formation include an acidic buffer and a component capable of serving as a lamellar silica template, as discussed above. Any of the formulation components discussed above can be used in the formulations tested for susceptibility to lamellar silica formation in a glass container. In embodiments, the pharmaceutical formulation filled in the glass container comprises sodium chloride, sodium citrate dihydrate, and polysorbate 80.

The method of screening can optionally include spiking the pharmaceutical formulation with known and preselected concentrations of silicon to induce lamellar silica formation more quickly as an accelerated testing condition. The spiked elemental silicon can be from a variety of sources, including for example, sodium silicates, $(Na_2SiO_2)_nO$. In embodiments, sodium metasilicate, $Na_2SiO_3$, is used as the source of the elemental silicon.

The pharmaceutical formulation may be spiked with a source of elemental silicon such that the resulting concentration of elemental silicon is about 1 ppm to about 50 ppm, about 2 ppm to about 45 ppm, about 5 ppm to about 30 ppm, about 10 ppm to about 25 ppm, or about 15 to about 20 ppm, for example about 1, 2, 5, 6, 7, 8, 9, 10, 12, 15, 18, 20, 22, 24, 26, 28, 30 35, 40, 45, or 50 ppm. In embodiments, the formulation is spiked with the source of elemental silicon such that the concentration of elemental silicon is up to about 30 ppm. In preferred embodiments, the formulation is spiked with a source of silicon such that the formulation has a concentration of about 5 ppm to about 10 ppm elemental silicon.

The filled glass containers are then stored for a period of time and checked at periodic time points for lamellar silica formation. The total storage time can range from about 1 day to about 180 days depending on the storage temperature. Other suitable storage times include about 10 days to about 150 days, about 14 days to about 90 days, about 20 days to about 60 days, or about 30 days to about 45 days. For example, suitable times include about 1 day, about 10 days, about 14 days, about 30 days, about 45 days, about 60 days, about 90 days, or about 180 days.

The filled glass containers may also be stored at various temperatures, with temperatures in excess of 40° C. representing accelerated conditions for many formulations. The filled glass containers may be stored at a temperature of about 0° C. to about 90° C., about 10° C. to about 75° C., about 20° C. to about 60° C., or about 30° C. to about 50° C., for example, about 0° C., about 10° C., about 20° C., about 30° C., about 40° C., about 50° C., about 60° C., about 75° C., or about 90° C. In various embodiments, the filled glass containers are stored at a temperature of 40° C. for at least 14 days.

After storage or at the pre-defined monitoring time points, the pharmaceutical formulation in the filled glass containers is optically analyzed for the formation of particles in the buffer. When particle formation is observed, one or more particles are isolated from the buffer for structural and elemental analysis to determine a morphology and chemical composition of the particle. The one or more isolated particles may be analyzed using one or more of optical microscopy, scanning electron microscopy/energy dispersive X-ray spectroscopy (SEM/EDS), Fourier-transform infrared spectroscopy (FTIR), x-ray photoelectron spectroscopy (XPS), differential interference contrast microscopy (DIC), microflow imaging (MFI), and combinations thereof.

Figure 1A:
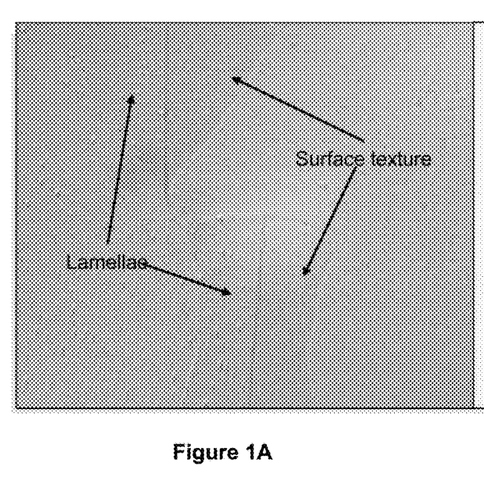
FIG. 1A is an SEM micrograph of the interior surface of a glass container showing disrupted surface texture as a result of conventional glass delamination.
Figure 1B:
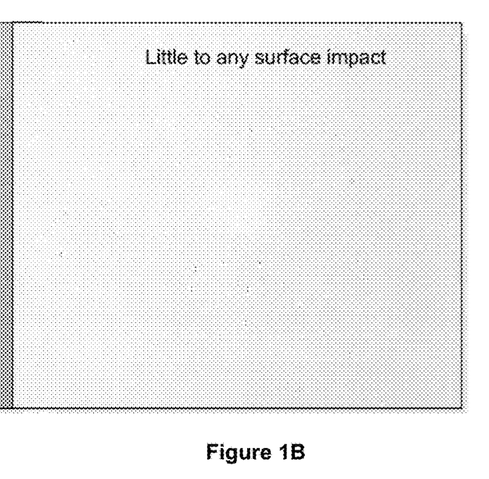
FIG. 1B is an SEM micrograph showing little to any impact to the surface texture of a glass container having lamellar silica.

Once the particles are isolated and the glass container is emptied, the interior surface of the glass container is also analyzed for delamination-type deformation of the interior surface. As used herein, the term "delamination-type deformation" of the interior surface of the glass container refers to the typical pitting, etching, corrosion, or otherwise disruption seen on the surface of the glass container due to the delamination of glass lamellae into the solution. For example, FIG. 1A is an SEM micrograph of the surface of a glass container that has undergone delamination. The interior surface of the glass container can be analyzed for delamination-type deformation as prescribed by USP Guidance <1660> Evaluation of the Inner Surface Durability of Glass Containers, or as taught by Haines et al in "Glass Flakes," Contract Pharma (2013), the entirety of which is incorporated herein by reference. Exemplary methods of analyzing the interior surface of the glass container include, but are not limited to, stereomicroscopy, secondary ion-mass spectrometry (SIMS) depth profiling, and scanning electron microscopy (SEM). In embodiments, the interior surface of the glass container is analyzed using one or more of stereomicroscopy, secondary ion-mass spectrometry (SIMS) depth profiling, and scanning electron microscopy (SEM).

If the presence of silicon, oxygen, and carbon is detected in the isolated particles in the absence of delamination-type deformation of the interior surface of the glass container, the glass container is considered susceptible to lamellar silica formation.

Figure 2A:
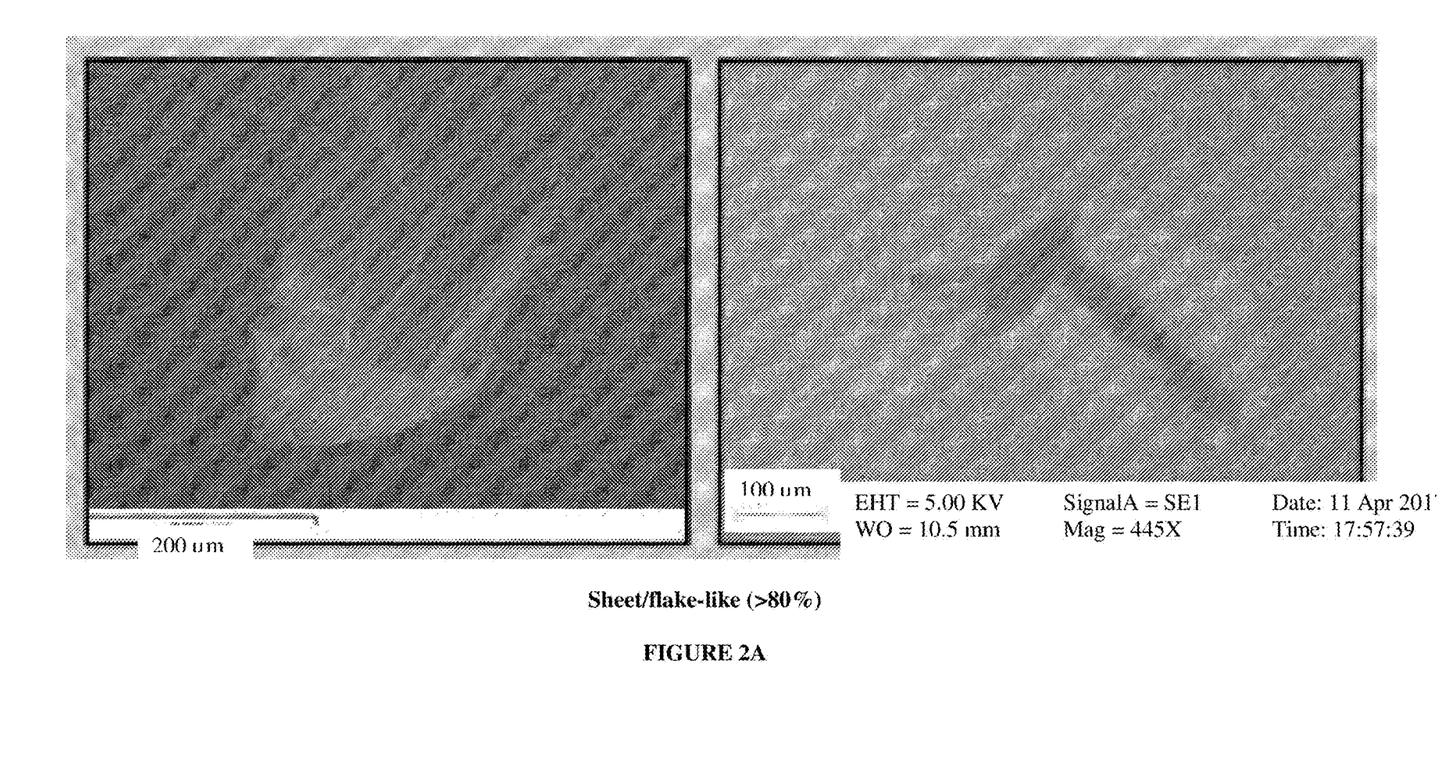
FIGS. 2A-C are SEM micrographs of observed morphologies of lamellar silica.
Figure 2B:
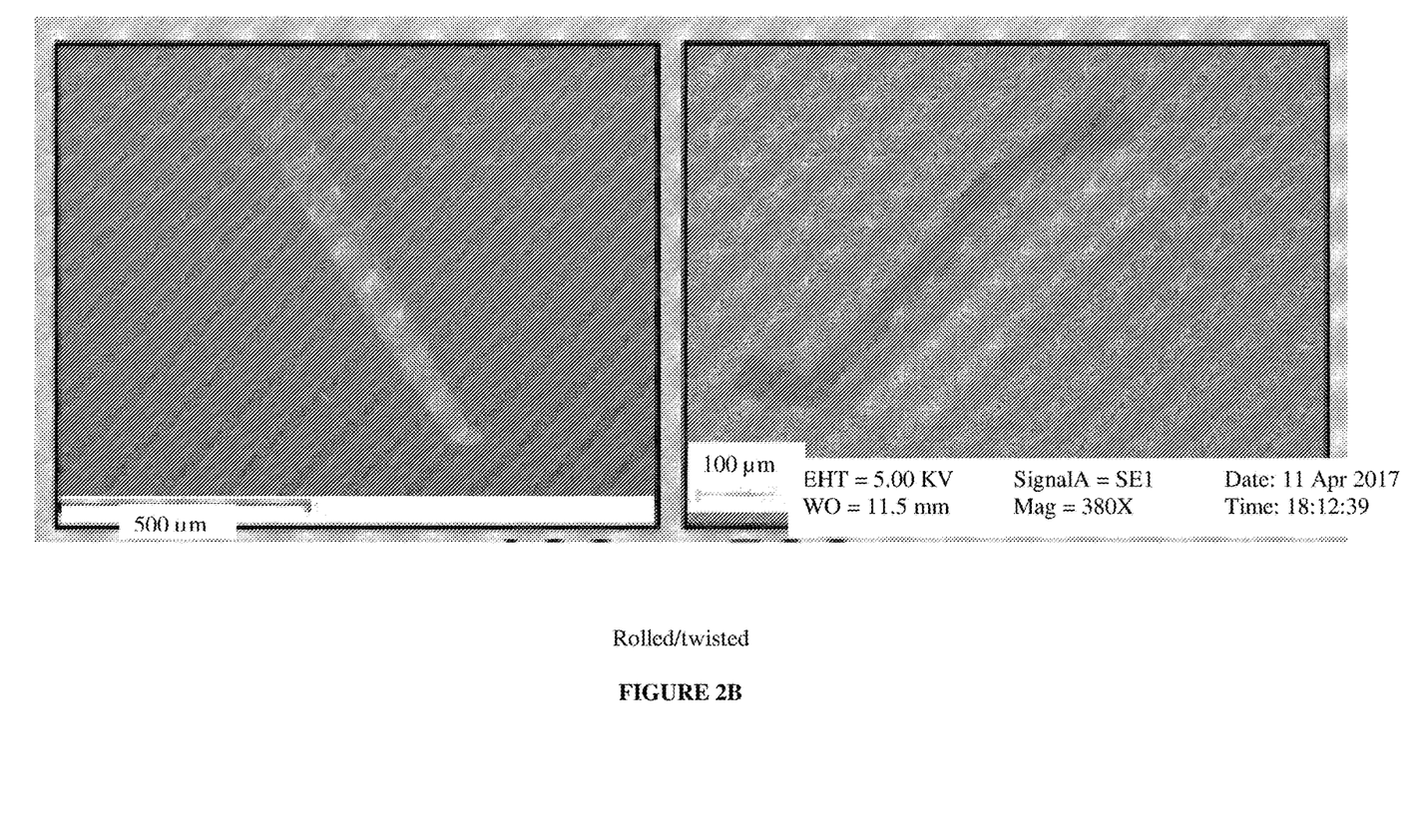
Figure 2C:
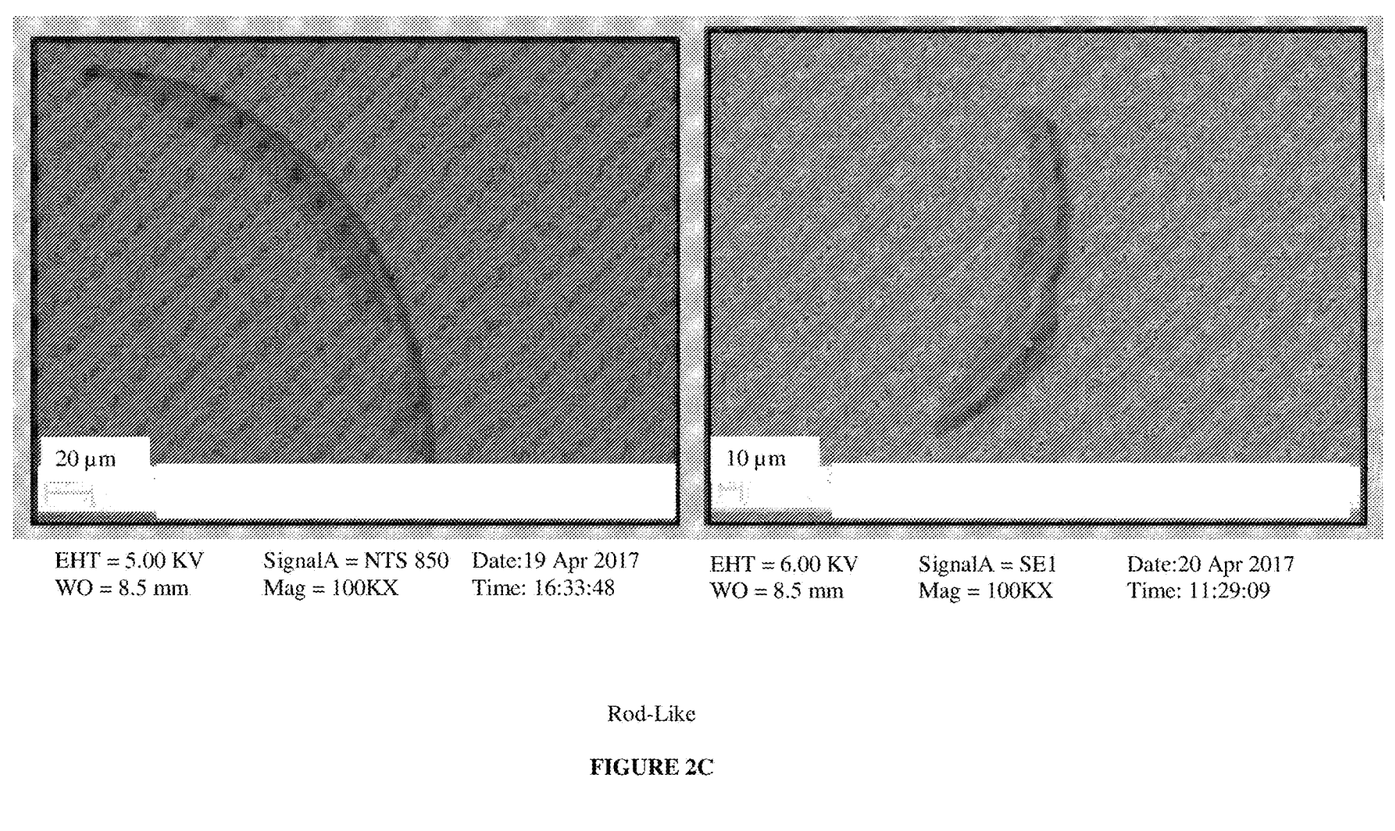

Generally, lamellar silica are thin and flake or sheet-like particles having an organic content. The flake or sheet-like shape can be rolled giving a rod-like or twisted appearance. For example, FIG. 2 illustrates three morphologies observed.

The following examples are provided to illustrate the methods of the disclosure, but are not intended to limit the scope thereof.

EXAMPLES

Example 1—Effect of the Container Storing the Pharmaceutical Formulation

Three types of vials were tested to determine if the composition of the container had an effect on the formation of lamellar silica in the pharmaceutical formulation.

Eighty (80) type 1b delamination-controlled borosilicate glass vials, three hundred and fifty-five (355) Crystal Zenith® (CZ) plastic vials, and three hundred and fifty-five (355) Corning Valor™ aluminosilicate glass vials were filled with a pharmaceutical formulation. Of each vial type, forty (40) were filled with a formulation spiked with a sodium metasilicate such that the formulation had a concentration of 10 ppm elemental silicon. The remaining vials were filled with pharmaceutical formulations containing no additional silica (i.e. the formulations had 0 ppm silicon). Prior to being filled, the type 1b delamination-controlled borosilicate glass vials and the Corning Valor™ aluminosilicate glass vials were washed and dried using standard batch process. The standard wash include 4 cycles of WFI rinsing at a temperature of at least 72° C. and a pressure of 10 psi for 1,000 ms. Vials were then dried for 8 cycles at 14.5 psi for 1,000 ms. After drying, all vials underwent depyrogenation in an oven at 250° C. with a ramp rate of 1.5° C./min. The CZ plastic vials were not washed or dried, as these vials are ready-to-use from the manufacturer.

All vials were stored at 40° C. for 14 days and inspected using an automated camera-based inspection method capable of detecting lamellar silica particles. Vials were inspected at 0 days (i.e. immediately upon filling), at 7 days, and at 14 days.

Figure 3:
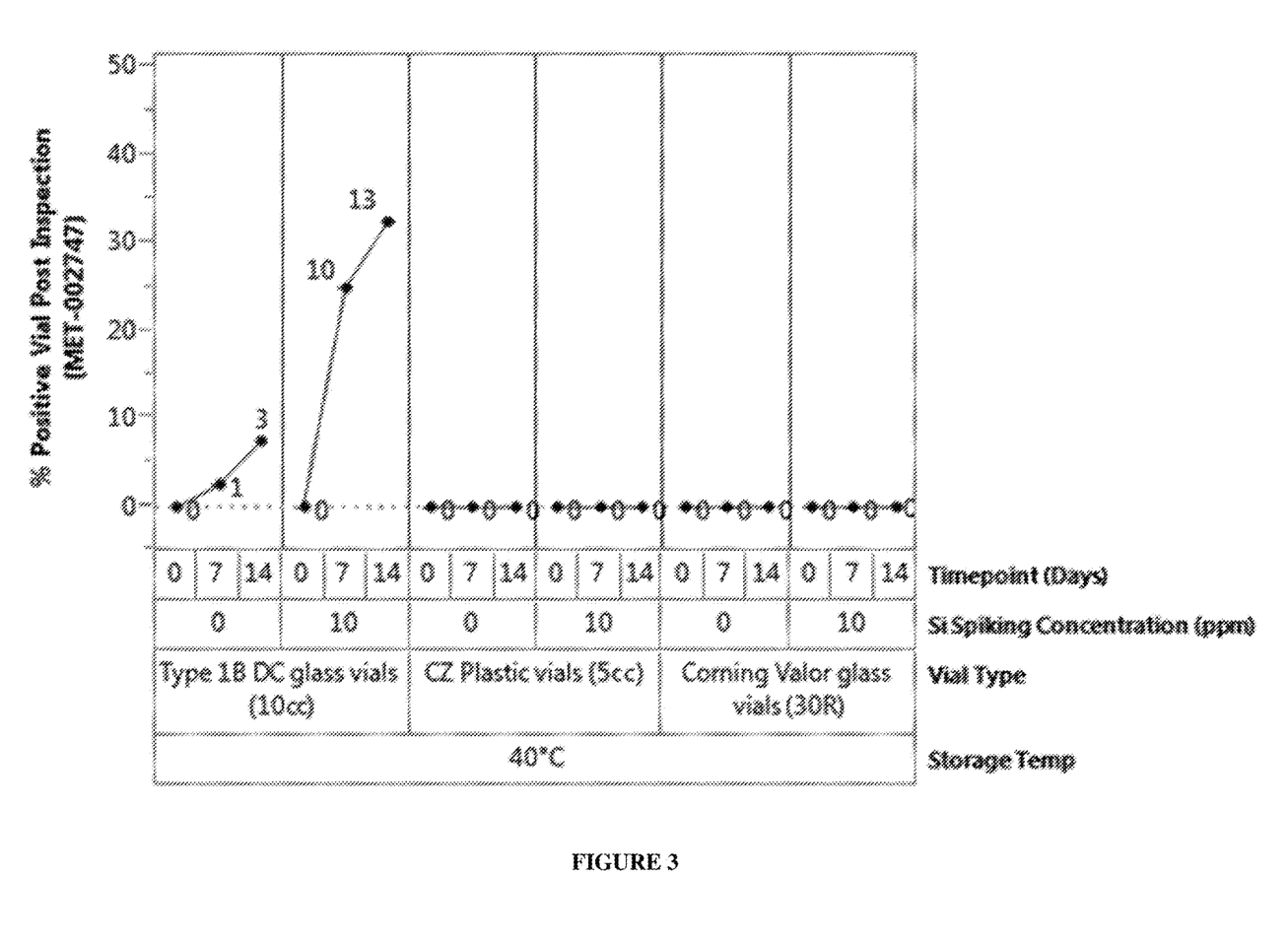
FIG. 3 is a graph showing the incidence of the formation of lamellar silica in pharmaceutical formulations contained within type 1b borosilicate glass containers, plastic containers, and aluminosilicate glass containers.

As can be seen in FIG. 3, no particles were detected in the plastic vials or in the aluminosilicate glass vials for either formulation after storage at 40° C. for 14 days. In contrast, after 7 days, 1% of the type 1b vials filled with the formulation alone showed particle formation, while 10% of the type 1b vials filled with the silica-spiked formulation showed particle formation. After 14 days, the percentage of these vials showing particle formation increased to 10% and 13%, respectively.

These results demonstrate the dependence of the formation of lamellar silica on glass containers made of borosilicate glass.

Example 2—Silicon Spiking Studies

Unwashed, standard washed, and vials washed and dried in accordance with an embodiment of the disclosure were filled with a pharmaceutical formulation that was spiked with various levels of elemental to induce particle formation. Sodium metasilicate was used as the source of elemental silicon. All vials were standard type 1b vials. Prior to being filled, vials were washed and dried under various conditions. The unwashed vials were filled as is, with no washing or drying steps. The standard washed vials underwent 4 cycles of WFI rinsing at a temperature of at least 72° C. and a pressure of 10 psi for 1,000 ms. Vials were then dried for 8 cycles at 14.5 psi for 1,000 ms. The extended wash vials underwent the same WFI conditions as the standard washed vials, but had a wash time of 6,000 ms and a dry time of 6,000 ms. After drying, all vials underwent depyrogenation in an oven at 250° C. with a ramp rate of 1.5° C./min. The vials were then filled with a pharmaceutical formulation. The pharmaceutical formulation included 10 mg/mL of the anti-CD20 antibody drug product in 154 mM sodium chloride, 25 mM sodium citrate dihydrate, and 0.07% (w/v) polysorbate 80, with a buffer pH of 6.5. Vials of each condition (unwashed, washed, and extended washed) were spiked with varying amounts of silica, stored at varying temperatures and inspected for lamellar silica formation over time.

Tables 1 and 2 display the results for the vials stored at temperatures of 25° C. and 40° C., respectively. The unwashed vials did not exhibit lamellar silica formation at both temperatures and at all observed time points. The vials of the standard wash showed significant amounts of lamellar silica formation at both temperatures and at all observed time points. The extended washed vials showed minimal lamellar silica formation, with only 1 vial showing lamellar silica when spiked with 5 ppm elemental silicon after 7 days at 40° C.

TABLE 1

Particle Formation Results for Vials stored at 25° C.

| Vial Condition | Si Spiking Concentration (ppm) | Vials per Condition | Vials with Particle Formation after 30 days |
|---|---|---|---|
| Unwashed | 0 | 40 | 0 |
|  | 5 | 25 | 0 |
|  | 10 | 40 | 0 |
|  | 30 | 40 | 0 |
| Standard Wash | 0 | 40 | 1 |
|  | 5 | 40 | 2 |
|  | 10 | 40 | 5 |
|  | 30 | 40 | 0 |
| Extended Wash | 0 | 34 | 0 |
|  | 5 | 34 | 0 |

TABLE 2

Particle Formation Results for Vials stored at 40° C.

| Vial Condition | Si Spiking Concentration (ppm) | Vials per Condition | Vials with Particle Formation after 7 days | Vials with Particle Formation after 14 days |
|---|---|---|---|---|
| Unwashed | 0 | 40 | 0 | 0 |
|  | 5 | 40 | 0 | 0 |
|  | 10 | 25 | 0 | 0 |
|  | 30 | 21 | 0 | 0 |
| Standard Wash | 0 | 39 | 1 | 3 |
|  | 5 | 36 | 4 | 5 |
|  | 10 | 30 | 10 | 13 |
|  | 30 | 38 | 2 | 3 |

TABLE 2-continued

Particle Formation Results for Vials stored at 40° C.

| Vial Condition | Si Spiking Concentration (ppm) | Vials per Condition | Vials with Particle Formation after 7 days | Vials with Particle Formation after 14 days |
|---|---|---|---|---|
| Extended | 0 | 28 | 0 | 0 |
| Wash | 5 | 33 | 1 | 1 |

This example demonstrates that extended washing and drying of the vials decreased the formation of lamellar silica, even when significant amounts of extraneous silicon was present in the pharmaceutical formulation. While the unwashed samples also did not exhibit lamellar silica formation, not washing vials for pharmaceutical use is not an acceptable practice in the industry. The resistance of the unwashed vials illustrates, however, the contribution of the standard wash procedures in the resulting lamellar silica formation.

Example 3—Effect of the Pharmaceutical Formulation

Figure 4:
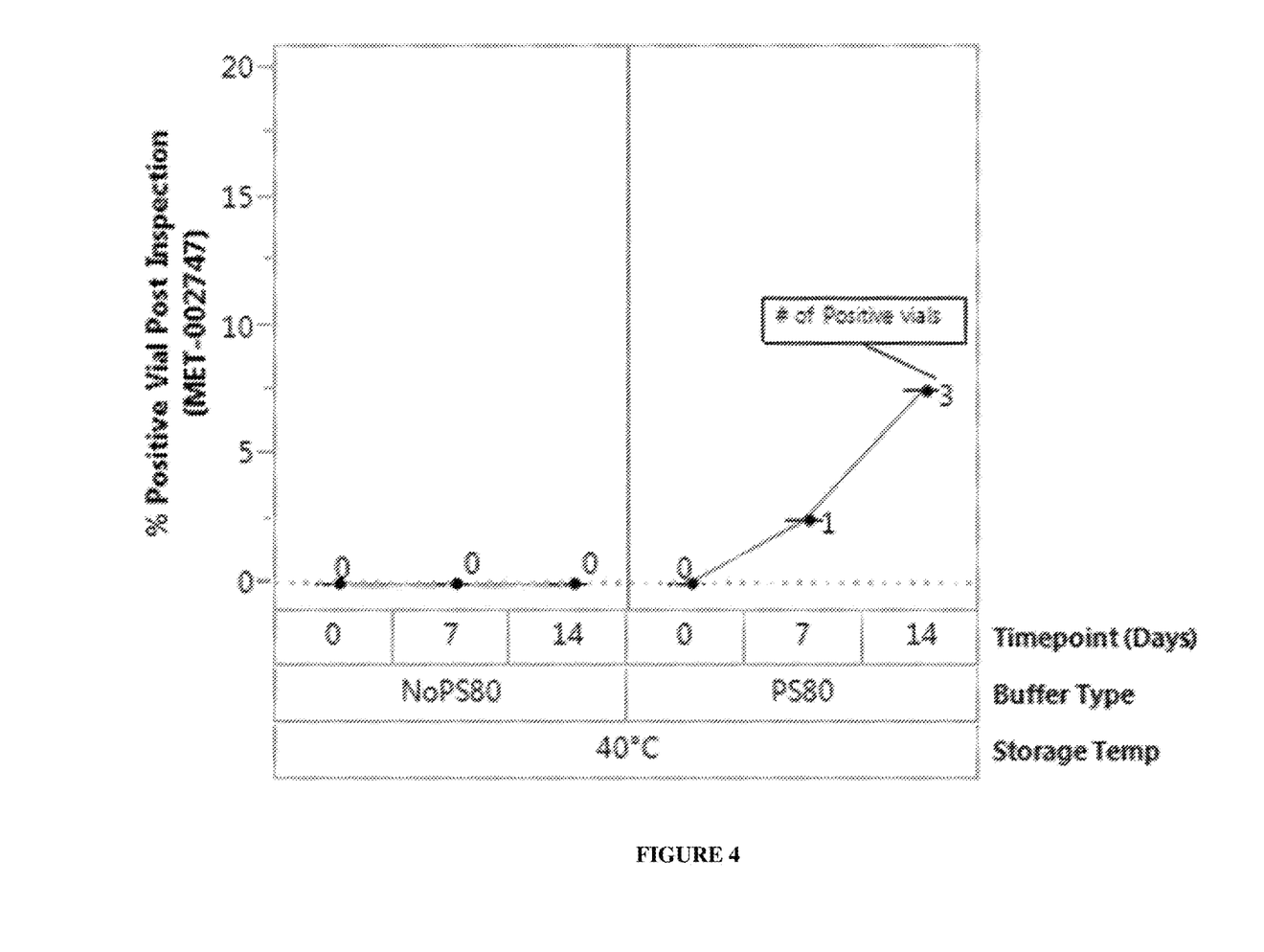
FIG. 4 is a graph showing the incidence of the formation of lamellar silica in glass containers containing a pharmaceutical formulation when polysorbate 80 is and is not present in the buffer.

Two sets of type 1b vials underwent standard washing and drying procedures (as described in Example 1). One set of the vials were filled with the a pharmaceutical formulation without active component that included 154 mM sodium chloride, 25 mM sodium citrate dihydrate, and 0.07% (w/v) polysorbate 80, with a buffer pH of 6.5. The second set of vials was filled with the same formulation, but without the 0.07% (w/v) polysorbate 80. Both sets of vials were stored at 40° C. for 30 days and inspected periodically for lamellar silica formation. Results of the study are shown in FIG. 4. This example demonstrates the dependence of the formation of lamellar silica on the components of the pharmaceutical formulation. Namely, without the inclusion of a template for the leached silica to aggregate into lamella, here polysorbate 80, lamellar silica did not form.

Example 4—Effect of the Duration of the Drying Cycle

Three lots of 10 cc vials (550 vials) and three lots of 50 cc vials (550 vials) were evaluated for formation of lamellar silica under standard wash and extended dry conditions in accordance with embodiments of the disclosure. All vials were standard type 1b borosilicate vials. All vials underwent four WFI rinse cycles at a temperature of at least 72° C. and 10 psi with each rinse lasting 1,000 ms. Vials then were subjected 8 cycles of drying, each with an extended drying time of 6,000 ms at 14.5 psi. All vials were then depyrogenated at 250° C. with a ramp rate of 1.5° C./min. Vials are then stored between 2° C. and 8° C. until time 0. As used herein, "time 0" refers to the time at which vials are transitioned from their long-term storage temperature of 2° C. to 8° C. to the appropriate temperature used to observe for the formation of lamellar silica. At time 0, the vials were stored at either 25° C. or 40° C. for 30 days. Vials stored at 25° C. were inspected at time points of 0 days (i.e. immediately upon removing from storage at 2° C. to 8° C.) and 30 days. Vials stored at 40° C. were inspected for particle formation at time points of 0, 7, 14, and 30 days.

At the end of 30 days, no vials of either size tested (10 cc and 50 cc) showed the formation of lamellar silica.

Example 5—Effect of Depyrogenation Conditions

Three lots of 10 cc vials (550 vials) and three lots of 50 cc vials (550 vials) were evaluated for formation of lamellar silica after undergoing a temperature hold in the depyrogenation oven prior to temperature ramping. All vials were a type 1b borosilicate glass. Vials underwent 4 cycles of WFI rinsing at a temperature of at least 72° C. and a pressure of 10 psi for 2,000 ms. Vials were then dried for 8 cycles at 14.5 psi for 6,000 ms. Vials were held in the depyrogenation oven at 90° C. for 60 mins before the depyrogenation cycle, which was set to 250° C. with a ramp rate of 1.5° C./min. Vials were then stored between 2° C. and 8° C. until time 0. At time 0, vials were stored at either 25° C. or 40° C. for 30 days. Vials stored at 25° C. were inspected at time points of 0 days and 30 days. Vials stored at 40° C. were inspected for particle formation at time points of 0, 7, 14, and 30 days.

At the end of 30 days, no vials of either size tested (10 cc and 50 cc) showed the formation of lamellar silica.

Example 6—Effect of the Duration of the Washing and Drying Cycles

Three lots of 10 cc vials (550 vials) and three lots of 50 cc vials (550 vials) were evaluated for formation of lamellar silica under a moderately extended wash and extended dry conditions. All vials were standard type 1b borosilicate vials. All vials underwent four WFI rinse cycles at a temperature of at least 72° C. and 10 psi with each rinse lasting 3,000 ms. Vials then underwent 8 cycles of drying, each with an extended drying time of 6,000 ms at 14.5 psi. All vials were then depyrogenated at 250° C. with a ramp rate of 1.5° C./min. Vials were then stored between 2° C. and 8° C. until time 0. At time 0, vials were stored at either 25° C. or 40° C. for 30 days. Vials stored at 25° C. were inspected at time points of 0 days and 30 days. Vials stored at 40° C. were inspected for particle formation at time points of 0, 7, 14, and 30 days.

At the end of 30 days, no vials of either size tested (10 cc and 50 cc) showed the formation of lamellar silica.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed:

1. A method of screening a glass container for storing a pharmaceutical formulation for susceptibility to lamellar silica formation when filled with the pharmaceutical formulation, comprising:
   filling a washed and depyrogenized glass container with a buffer for the pharmaceutical formulation, wherein the glass container comprises ions selected from the group comprising sodium, calcium, hydroxide, silicate, and combinations thereof;
   storing the filled glass container at a temperature of 40° C. for at least 14 days;
   optically analyzing the buffer after storage for formation of one or more particles in the buffer;
   when particle formation is observed, isolating the one or more particles from the buffer for structural and elemental analysis;
   analyzing the isolated one or more particles using one or more of optical microscopy, scanning electron microscopy/energy dispersive X-ray spectroscopy (SEM/EDS), Fourier-transform infrared spectroscopy (FTIR), x-ray photoelectron spectroscopy (XPS), differential interference contrast microscopy (DIC), microflow imaging (MFI), and combinations thereof to determine a morphology of the particles and chemical composition; and
   analyzing an interior surface of the glass container, once emptied and after isolating the one or more particles, for delamination-type deformation of the interior surface, wherein the presence of particles having a chemical composition comprising silicon, oxygen, and carbon, and an absence of the delamination-type deformation of the interior surface of the glass container indicates the susceptibility to lamellar silica formation.

2. The method of claim 1, wherein the glass container is a borosilicate glass container.

3. The method of claim 1, wherein the interior surface of the glass container is analyzed using one or more of stereo-microscopy, secondary ion-mass spectrometry (SIMS) depth profiling, and scanning electron microscopy (SEM).

4. The method of claim 1, wherein the buffer comprises one or more of citric acid, phosphoric acid, acetic acid, succinic acid, gluconic acid, histidine, polysorbate 80, polysorbate 20, hyaluronic acid, pluronic acid, sodium alginate, gelatin, chitosan, lecithin, mannitol, sucrose, sulfobutylether beta cyclodextrin, and sodium chloride.

5. The method of claim 1, further comprising spiking the buffer with between 5 and 10 ppm elemental silicon.

6. The method of claim 1, wherein the buffer comprises one or more of citric acid, phosphoric acid, acetic acid, and salts thereof.

* * * * *